(12) United States Patent
Huang

(10) Patent No.: US 10,272,193 B2
(45) Date of Patent: Apr. 30, 2019

(54) EMERGENT CARDIAC KIT AND DELIVERY DEVICE FOR TREATING MYOCARDIAL INFARCTION COMPLICATED BY ADVANCED HEART FAILURE

(71) Applicant: Ming-He Huang, League City, TX (US)

(72) Inventor: Ming-He Huang, League City, TX (US)

( * ) Notice: Subject to any disclaimer, the term of this patent is extended or adjusted under 35 U.S.C. 154(b) by 159 days.

(21) Appl. No.: 15/224,811

(22) Filed: Aug. 1, 2016

(65) Prior Publication Data

US 2017/0028125 A1 Feb. 2, 2017

Related U.S. Application Data

(60) Provisional application No. 62/199,310, filed on Jul. 31, 2015.

(51) Int. Cl.
| | |
|---|---|
| *A61M 37/00* | (2006.01) |
| *A61M 31/00* | (2006.01) |
| *A61M 5/14* | (2006.01) |
| *A61M 5/19* | (2006.01) |
| *A61M 5/34* | (2006.01) |
| *A61M 25/00* | (2006.01) |

(52) U.S. Cl.
CPC ............ *A61M 5/1407* (2013.01); *A61M 5/19* (2013.01); *A61M 5/34* (2013.01); *A61M 25/0028* (2013.01)

(58) Field of Classification Search
CPC .......... A61M 2005/3139; A61M 5/315; A61M 3/005; A61M 5/1408; A61M 5/1456; A61M 5/3137
See application file for complete search history.

(56) References Cited

U.S. PATENT DOCUMENTS

| | | | | |
|---|---|---|---|---|
| 4,044,757 | A  * | 8/1977 | McWhorter | A61M 3/0262 600/432 |
| 6,936,033 | B2 * | 8/2005 | McIntosh | A61B 17/00491 604/191 |
| 2002/0128206 | A1* | 9/2002 | Hay | C07D 209/20 514/11.1 |
| 2003/0233067 | A1 | 12/2003 | McIntosh et al. | |
| 2005/0187278 | A1 | 8/2005 | Taylor | |

FOREIGN PATENT DOCUMENTS

| | | |
|---|---|---|
| RU | 2007122038 A | 12/2008 |
| WO | 2013063476 A1 | 5/2013 |

* cited by examiner

*Primary Examiner* — Rebecca E Eisenberg

(74) *Attorney, Agent, or Firm* — Benjamin Aaron Adler

(57) ABSTRACT

Provided herein are devices for concurrent intravenous infusion of multiple drugs. The device comprises a body with a syringe holding portion and a syringe driving portion, two or more syringes secured therein and a multi-lumen catheter with a plurality of inlet channels and a single outlet channel. Also provided is a method for treating acute myocardial infarction complicated by advanced acute heart failure in a patient. Two or more drugs, such as a beta-blocker and a positive inotropic agent, in prefilled syringes are secured in the device and administered simultaneously into a single vein in a patient without the drugs mixing prior to administration. In addition, a kit is provided that comprises the device and syringes prefilled with a beta-blocker and the positive inotropic agent.

9 Claims, 3 Drawing Sheets

EMERGENT CARDIAC KIT AND DELIVERY DEVICE FOR TREATING MYOCARDIAL INFARCTION COMPLICATED BY ADVANCED HEART FAILURE

CROSS-REFERENCE TO RELATED APPLICATIONS

This non-provisional application claims benefit of priority under 35 U.S.C. § 119(e) of provisional application U.S. Ser. No. 62/199,310, filed Jul. 31, 2015, the entirety of which is hereby incorporated by reference.

BACKGROUND OF THE INVENTION

Filed of the Invention

The present invention relates generally to the fields intravenous administration of drug combinations and medical devices. More specifically, the present invention is directed to devices and methods that enable simultaneous administration of multiple drugs, such as drugs for treating acute myocardial infarction complicated with advanced acute heart failure, via a single vein access while preventing the drug-drug interactions before administration.

Description of the Related Art

Concurrent infusion of multiple drugs has become a common practice in intravenous therapy when drugs need to be administered to a patient concurrently and may encounter undesired chemical reactions when mixed outside of the patient's body. The general procedure of concurrent infusion involves gaining access to one vein for each drug, and coordinated simultaneous infusion by a technician/nurse for each drug. However, this method requires multiple veins of a patient to be cannulated simultaneously. This technique, however, increases the pain caused by this procedure to the patient. Secondly, often, for many patients, especially obese patients with poor venous access, locating multiple veins within a short period of time can be challenging. This is particular true when medications need to be administered urgently such as in patients with acute myocardial infarction when time is the muscle. Delay in treatment represents loss of heart muscle mass with increased in-hospital mortality and adverse long-term outcome even they survive the acute heart attack. Thirdly, coordinating multiple technicians/nurses to simultaneously inject each of the drugs can be difficult. It may require extensive training with same group of technicians/nurses to finally achieve the concurrent infusion. Hence, the existing procedure is considered as defective for its low efficiency and high costs.

Therefore, there is a recognized need for a device and a method that enables that one technician/nurse performs concurrent infusion for multiple drugs in a timely manner using one vein of the patient, and preventing adverse reactions from drug-drug mixing before administration. The prior art is deficient in these aspects. The present invention fulfills this long standing need and desire in the art.

SUMMARY OF THE INVENTION

The present invention is directed to a device for device for concurrent intravenous infusion of multiple drugs. The device comprises a body having a syringe holding portion and a syringe driving portion and two or more syringes secured by the holding portion and said driving portion. A related device further comprises a multi-lumen catheter having a plurality of inlet channels and a single outlet channel comprising a plurality of lumens each of which is disposed in a watertight connection to one of the inlet channels and a plurality of Luer-hubs each with a distal end connected to one of the inlet channels and with a proximal end connected to a syringe hub.

The present invention also is directed to a device for concurrently administering multiple drugs intravenously. The device comprises a backboard with an open channel therethrough, a piston-like rod slidable through the channel and a multi-lumen catheter. The backboard comprises a plurality of syringe holders disposed on a top surface thereof each shaped to securely receive a syringe therein, a flange-like stop disposed in perpendicular relation to a distal end of the backboard and extending upwardly from the top surface of the backboard and downwardly from a bottom surface of the backboard and a first flange downwardly extending from the bottom surface of the backboard in parallel relation to and proximal to the downwardly extending flange-like stop. The piston-like rod comprises a proximal end slidably disposed within the open channel and a distal end having a plunger clip disposed thereon. The multi-lumen catheter comprises a plurality of inlet channels, a single outlet channel with a plurality of lumens each of which is disposed in a watertight connection to one of the inlet channels; and a plurality of Luer-hubs each with a distal end connected to one of the inlet channels.

The present invention is directed further to a method for treating acute myocardial infarction complicated by advanced acute heart failure in a patient. The method comprises securing at least two syringes prefilled with pharmacologically effective amounts of at least one beta-blocker and at least one positive inotropic agent into the device as described herein and administering simultaneously the at least one beta-blocker and the at least one positive inotropic agent into a vein of the patient.

The present invention is directed further still to a kit for protecting the heart and for treating acute myocardial infarction complicated by advanced acute heart failure in a patient. The kit comprises the device as described herein, a first syringe prefilled with a beta-blocker compound and a second syringe prefilled with a positive inotropic agent.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
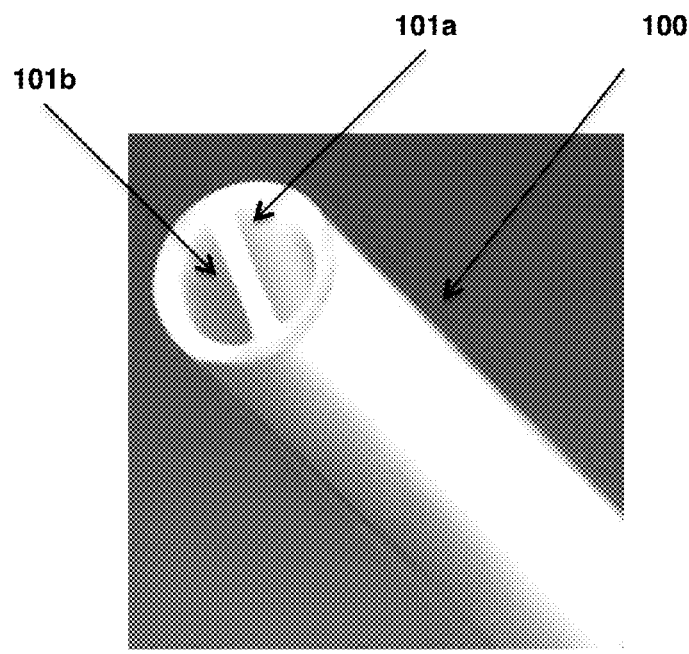
FIG. 1 is a cross-sectional view of a double-lumen catheter used in the device for simultaneous infusion of two different drugs.

As used herein in the specification, "a" or "an" may mean one or more.

As used herein in the claim(s), when used in conjunction with the word "comprising", the words "a" or "an" may mean one or more than one.

As used herein "another" or "other" may mean at least a second or more of the same or different claim element or components thereof. Similarly, the word "or" is intended to include "and" unless the context clearly indicates otherwise. "Comprise" means "include."

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

In one embodiment of the present invention, there is provided a device for concurrent intravenous infusion of multiple drugs, comprising a body having a syringe holding portion and a syringe driving portion; and two or more syringes secured by said holding portion and said driving portion. Further to this embodiment, the device comprises a multi-lumen catheter having a plurality of inlet channels and a single outlet channel comprising a plurality of lumens each of which is disposed in a watertight connection to one of the inlet channels; and a plurality of Luer-hubs each with a distal end connected to one of the inlet channels and with a proximal end connected to a syringe hub.

In both embodiments, the syringe holding portion may comprise a backboard having an open channel formed along a length of a bottom surface thereof; two or more syringe holders formed on a top surface of the backboard each having a shape to securely receive a syringe barrel therein; a flange-like motion stop disposed in perpendicular relation to a distal end of the backboard and extending upwardly from the top surface of the backboard and downwardly from a bottom surface of the backboard; and a first flange downwardly extending from the bottom surface of the backboard in parallel relation to and proximal to the downwardly extending motion stop. In these embodiments the flange-like motion stop may form a gap with each distal end of the syringe holders into which a barrel flange of the syringe is secured. Also the first flange may comprise a concavity at a lower end thereof configured to support a finger of a user of the device.

Also in both embodiments the syringe driving portion may comprise a rod having a proximal end disposed within the open channel of the backboard and slidable therethrough; and a plunger clip disposed on a distal end of the rod configured to secure a thumb end of a syringe plunger. In these embodiments the plunger clip may comprise a thumb plate disposed on the distal end of the rod and perpendicular to a longitudinal axis of the rod and a second flange extending upwardly from the rod in proximal and parallel relation to the thumb plate. Also, the thumb plate and the second flange may form a gap into which the thumb end of the plunger is secured.

In yet another embodiment of the present invention, there is provided device for concurrently administering multiple drugs intravenously, comprising a backboard with an open channel therethrough comprising a plurality of syringe holders disposed on a top surface thereof each shaped to securely receive a syringe therein; a flange-like stop disposed in perpendicular relation to a distal end of the backboard and extending upwardly from the top surface of the backboard and downwardly from a bottom surface of the backboard; and a first flange downwardly extending from the bottom surface of the backboard in parallel relation to and proximal to the downwardly extending flange-like stop; a piston-like rod comprising a proximal end slidably disposed within the open channel; and a distal end having a plunger clip disposed thereon; and a multi-lumen catheter comprising a plurality of inlet channels; a single outlet channel with a plurality of lumens each of which is disposed in a watertight connection to one of the inlet channels; and a plurality of Luer-hubs each with a distal end connected to one of the inlet channels. Further to this embodiment the device comprises a plurality of syringes disposed within the syringe holders and secured by the plunger clip, the syringes each connectable to a proximal end of the Luer-hubs.

In both embodiments the flange-like stop may be gapped with distal ends of the syringe holders to securably receive a barrel flange of a syringe. Also, the first flange may comprise a concavity at a lower end thereof configured to support a finger of a user of the device. In addition in both embodiments the plunger clip may comprises a thumb plate disposed in perpendicular relation to a longitudinal axis of the rod and a second flange extending upwardly from the rod in proximal and parallel relation to the thumb plate. Furthermore, the thumb plate may be gapped with the second flange to securably receive a thumb end of a syringe plunger.

In yet another embodiment of the present invention, there is provided a method for treating acute myocardial infarction complicated by advanced acute heart failure in a patient, comprising the steps of securing at least two syringes prefilled with pharmacologically effective amounts of at least one beta-blocker and at least one positive inotropic agent into the device as described supra; and administering simultaneously the at least one beta-blocker and the at least one positive inotropic agent into a vein of said patient. In this embodiment, the beta-blocker and positive inotropic agent do not mix before entering the patient's vein. Representative examples of the beta-blocker include but are not limited to Acebutorol, Atenolol, Betaxol, Carteolol, Carvedilol, Esmolol, Labetalol, Landiolol, Metoprolol, Nadolol, Nebivolol, Oxprenolol, Penbutolol, Pindolol, Propanolol, Timolol or a combination thereof. Representative examples of positive inotropic agent include but are not limited to a PDE-3 inhibitor, Dobutamine, Dobutamine, Isoproterenol, Epinephrine, Levosimendan or a combination thereof. A PDE-3 inhibitor comprises Amrinone, Cilostazol, Milrinone, Enoximone or a combination thereof.

In yet another embodiment of the present invention, there is provided a kit for protecting the heart and for treating acute myocardial infarction complicated by advanced acute heart failure in a patient, comprising the device as described supra; a first syringe prefilled with a beta-blocker compound; and a second syringe prefilled with a positive inotropic agent. The beta-blocker and positive inotropic agent are as described supra.

Provided herein are devices, systems, kits and methods for concurrent infusion of multiple drugs using one access point of a patient's vein. Generally, the device has a body or structure that comprises portions or components configured to hold a plurality of syringes and to drive the plungers thereof and a multi-lumen catheter in fluid connection with the syringes. The multi-lumen catheter may comprise a single outlet channel with a plurality of divided or separated orifices or lumens and a plurality of inlet channels which prevents mixing of the drugs in the syringes and unwanted drug-drug interactions. The inlet channels may be color coded for identification of any drug contained therein. The combination of the device with the multi-lumen catheter comprises a drug delivery system when connected to two or more syringes.

In use the device enables the controlled, simultaneous delivery of multiple drugs to a patient via a single vein with a single controlled motion by one administering the drugs. Thus the device is useful in the treatment of pathophysiological conditions requiring concurrent administration of multiple drugs. For example, the device may be used in treating acute myocardial infarction complicated by advanced acute heart failure or generally for protecting the heart. The device may be used in the administration or infusion of any drugs deliverable via intravenous injection. Efficacious drugs in the instance of acute myocardial infarction as described herein may be beta-blockers and positive inotropic agents as are known in the art. Representative beta-blockers, include but are not limited, to Acebutorol, Atenolol, Betaxol, Carteolol, Carvedilol, Esmolol, Labetalol, Landiolol, Metoprolol, Milrinone, Nadolol, Nebivolol, Oxprenolol, Penbutolol, Pindolol, Propanolol, and Timolol. Representative positive inotropic agents include, but are not limited to, PDE-3 inhibitor (Amrinone, Cilostazol, Milrinone and Enoximone), Dobutamine, Dobutamine, Isoproterenol, Epinephrine, and Levosimendan. One of ordinary skill in the art is well able to determine which drugs and the amounts to infuse or administer depending on the condition to be treated and the patient.

Particularly, the device or system of the present invention is used to apply concurrent emergent intravenous infusion of the beta-blocker and positive inotropic agent via a single venous access to treat acute myocardial infarction in patients associated with advanced acute heart failure. Acute heart failure in acute myocardial infarction patients is classified according to the Killip classification (I, II, III and IV). Killip I represents no heart failure. Class IV represents the worst heart failure. Nearly 30% patients with acute myocardial infarction present with Killip II to IV heart failure. The in-hospital mortality rate of Killip IV patients is up to 69% in the elderly group and 54% in the 65-74 age group.

Beta-blocker administration during acute myocardial infarction is effective in reducing infarct-size associated with improved long-term outcome and survival in patient with Killip I class. However, beta-blockers also can exert harmful effects on already weakened heart muscle in acute myocardial infarction patients with advanced heart failure (Killip III and IV). This undesirable side effect of beta-blocker is termed negative inotropic effect. In acute myocardial infarction patients with higher Killip class heart failure, beta-blocker can further weaken heart muscle performance resulting in a worsened clinical course associated with an increased death rate.

The present invention provides a method for overcoming a beta-blocker's negative inotropic effect while preserving its infract-size limiting benefit in acute myocardial infarction patients by concurrent intravenous infusion of a positive inotropic agent that augments heart muscle contraction with a beta-blocker. Moreover, the method further enhances heart contractile function resulting in better recovery with potential reduction of in-hospital mortality. Hence, administering a beta-blocker and a positive inotropic agent using the device as described herein is a quick and convenient way of treating acute myocardial infarction patients presenting with advanced Killip class heart failure.

Kits of the present invention comprise the device for concurrent infusion of multiple drugs as described herein. The kit may include the multi-lumen catheter. The kit contains two or more syringes each pre-filled with a different drug.

Particularly, embodiments of the present invention are better illustrated with reference to the Figure(s), however, such reference is not meant to limit the present invention in any fashion. The embodiments and variations described in detail herein are to be interpreted by the appended claims and equivalents thereof.

FIG. 1 depicts a double-lumen catheter that is utilized with the device. The catheter 100 comprises a pair of non-communicating vascular access lumens 101a,b to prevent undesired drug interactions before the drugs enter the vein. A non-limiting representative example of the material from which the catheter is formed is polyurethane or other material biocompatible for medical use. The catheter has an outer diameter from about 2 mm to about 3 mm and a length of about 15 cm to about 30 cm (about 6 inches to about 12 inches).

Figure 2:
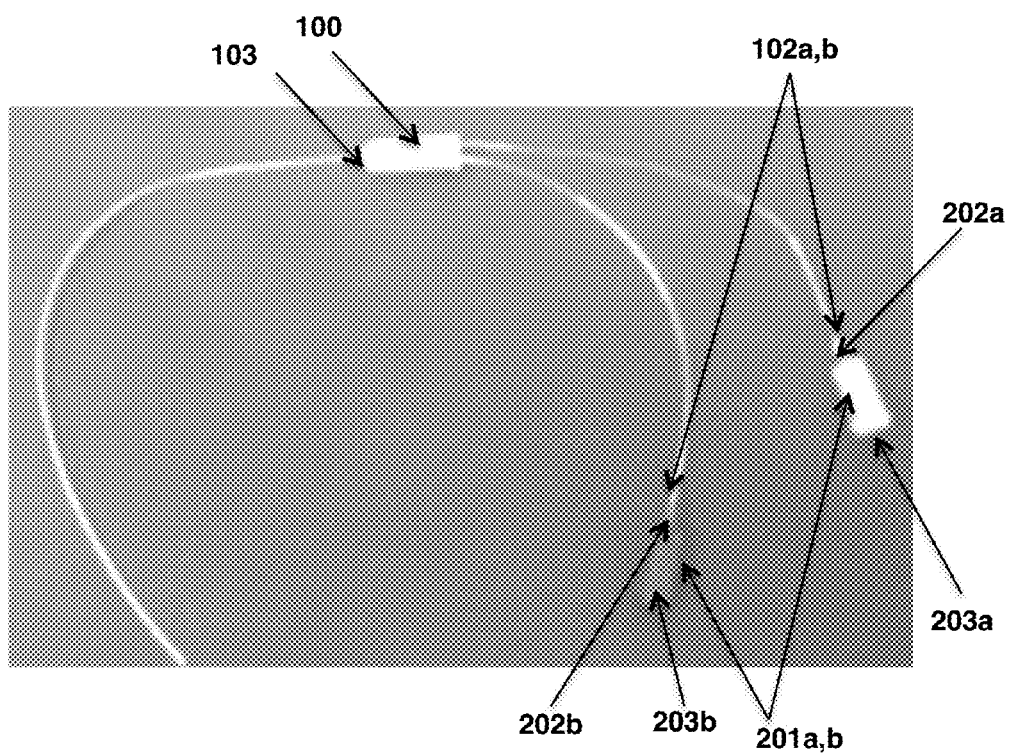
FIG. 2 shows the structure of the catheter with two inlet ends and one outlet end with two separate orifices.

FIG. 2 illustrates the arrangement of the double-lumen catheter 100 with a pair of Luer-hubs 201a,b. The two inlet ends 102a,b of the catheter are fluidly connected to the outlets 202a,b of the Luer-hubs. Also shown is the single outlet channel 103 on the catheter. The inlets 203a,b of the Luer-hubs are directly, fluidly connectable to the outlets of two syringes.

Figure 3:
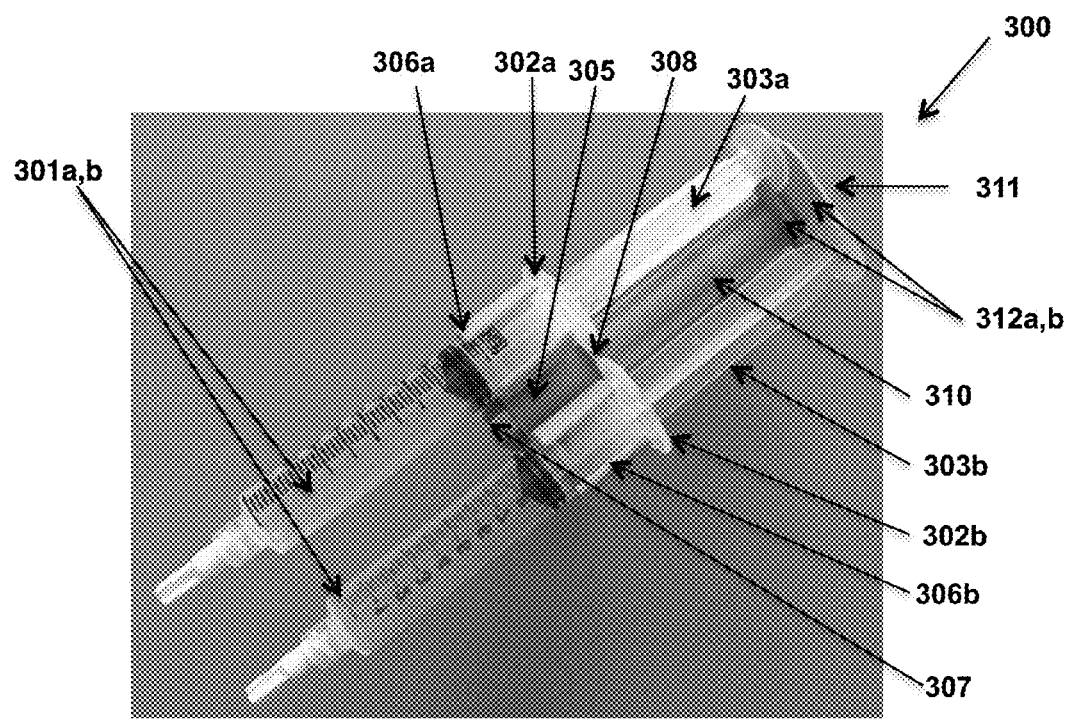
FIG. 3 is a front perspective view of the device illustrating how syringes are secured therein.

FIG. 3 illustrates how syringes are secured into the device. As depicted in this front perspective view, the device 300 comprises a backboard 305 (see FIG. 4) from which channels are formed as syringe holders 306a,b. The backboard has an open channel 307 disposed along the bottom surface. The backboard comprises a syringe motion stop 308 disposed on the backboard. The stop is flange-like in structure and is perpendicular to the surface of the backboard and extends upwardly from the top surface of the backboard and downwardly from the bottom surface (see FIG. 4). The stop is spaced from or forms a gap with the distal ends of the syringe holders at a width or diameter sufficient to secure the barrel flanges 302a,b of the syringes 301a,b therebetween. This enables syringes containing different amounts of drug to be held in position (see FIG. 6) so that the thumb ends of the plungers 303a,b uniformly abut the thumb plate 312a (described below) for simultaneous injection and prevents movement of the syringes when the plungers are in motion. The backboard comprises a first downwardly extending flange 309 (not shown, see FIG. 4).

A piston-like rod or structure 310 has a proximal end thereof disposed in the open channel in the backboard and is movable back and forth therethrough along its length in a piston-like motion. The distal end of the piston-like rod is a plunger stabilizer and comprises a plunger clip 311. The plunger clip has a thumb plate 312a disposed at the distal end of the piston-like rod and perpendicular to the longitudinal axis of the rod and a second flange which is an upwardly extending thumb plunger flange 312b disposed on the rod in parallel to and proximal to the thumb plate. The gap or space between the thumb plate and the thumb plunger flange has a diameter sufficient to clip, secure or lock the thumb ends of the plungers therein. This enables both drugs to be delivered at the same rate since the plungers are moved together.

Figure 4:
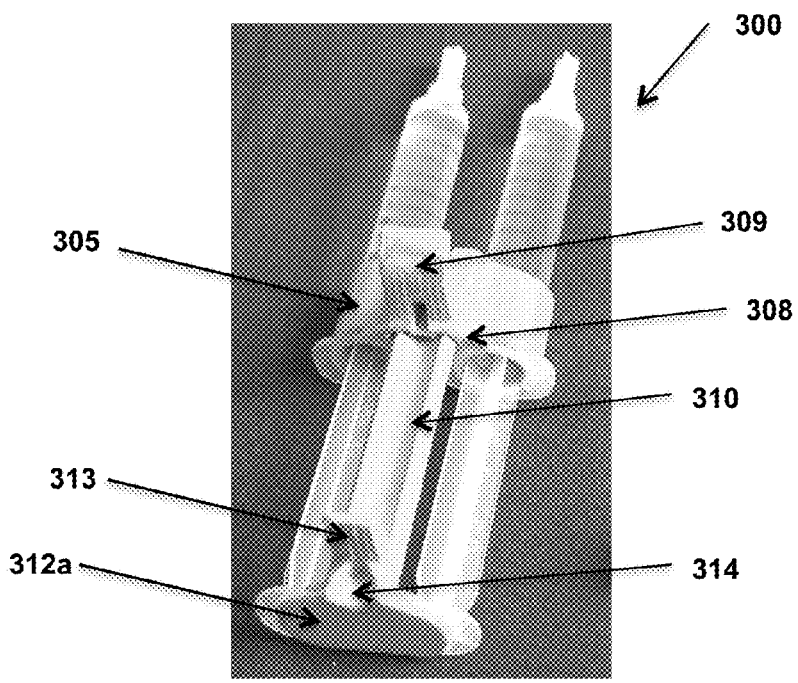
FIG. 4 is a back perspective view of the device of FIG. 3

With continued reference to FIG. 3, FIG. 4 is a perspective view of the back of the device. The first downwardly extending flange 309 is disposed on the device 300 on the back of the backboard 305 proximate to the syringe motion stop 308. The second flange forms a concavity at the lower end shaped to receive a finger of a user of the device. The device comprises a third downwardly extending, substantially flat flange 313 disposed on the back of the piston-like rod 310 in parallel to and proximal to the thumb plate 312a. A depression or rest 314 is formed between the bottom edge of the thumb plate and the distal surface of the thumb plate for positioning of the thumb when pressure is exerted against the thumb plate by a user of the device.

Figure 5:
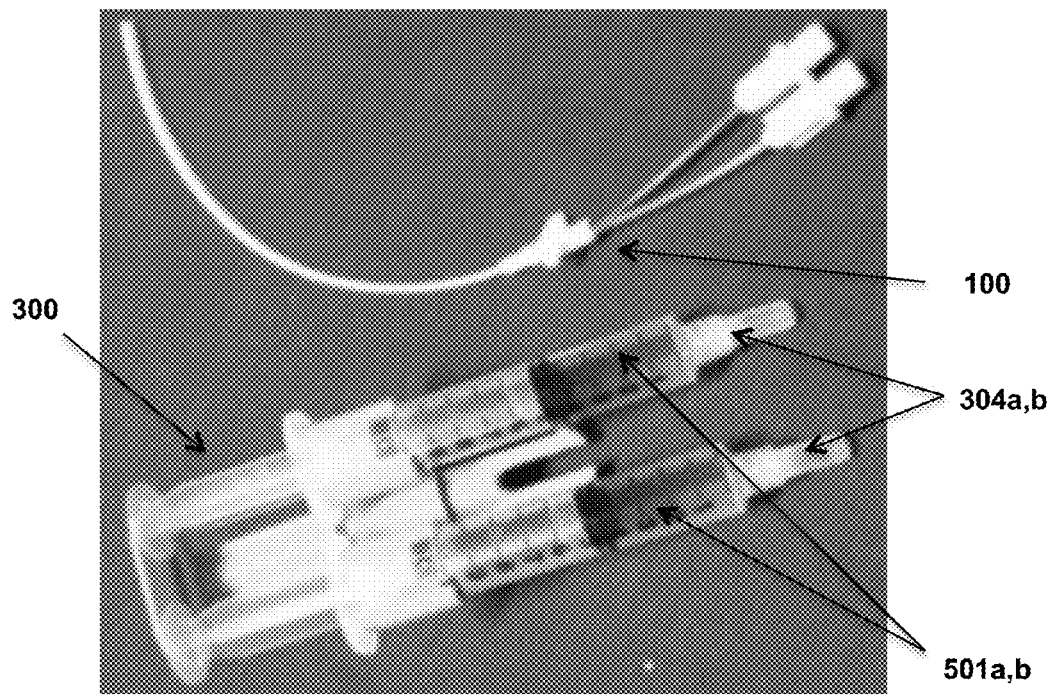
FIG. 5 depicts the device securing prefilled syringes and the multi-lumen catheter.

FIG. 5 shows the device and a double-lumen catheter comprising a drug delivery system. The device 300 secures syringes each filled with a drug 501a,b. Caps 304a,b are secured over the syringe hubs when the catheter is not attached.

Figure 6:
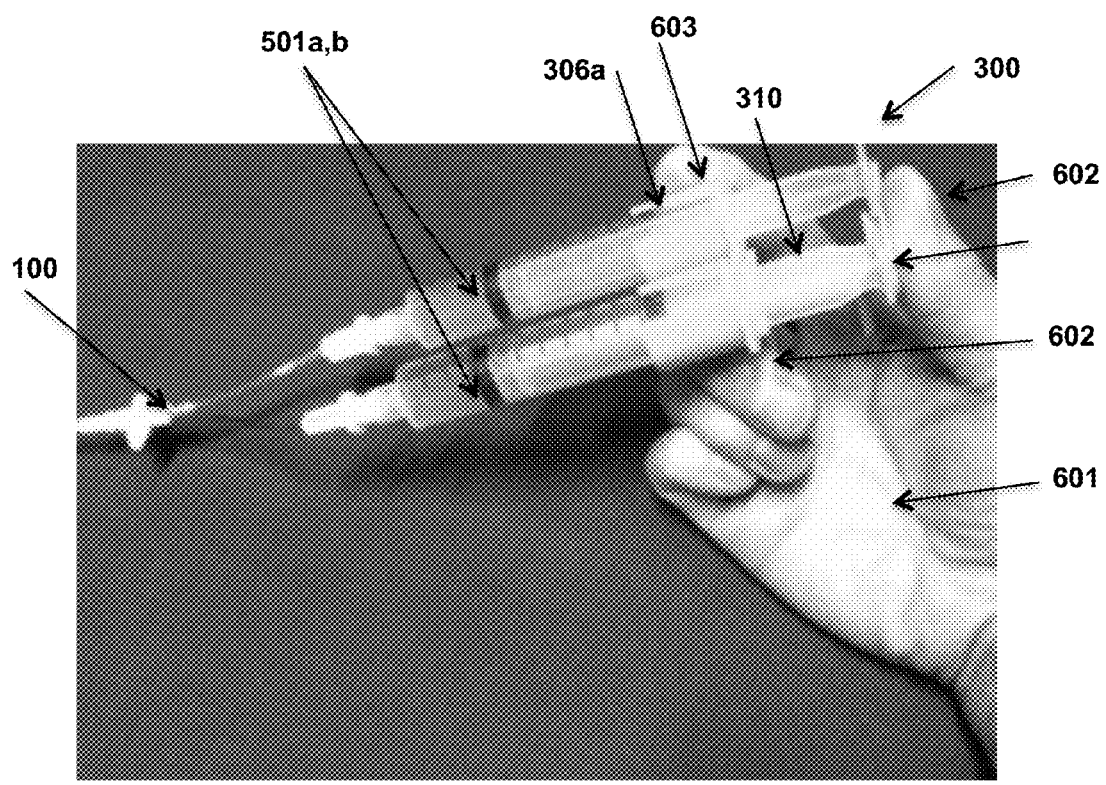
FIG. 6 illustrates a user holding the device to simultaneously infuse the drugs loaded into the prefilled syringes.

With continued reference to FIGS. 4-5, FIG. 6 illustrates the device in use. The device 300 contains 2 syringes 501a,b filled with different amounts of drugs. One syringe is loaded with an amount of a beta-blocker and the other syringe is loaded with a different amount of a positive inotropic agent. The syringes are mounted on the device. The device is configured such that when the syringes are secured in the syringe holders with the barrel flanges secured in the motion stop (see FIG. 3), the plungers, despite the difference in the amount of retraction, are easily secured in the plunger clip for simultaneous delivery of the drugs through the double-lumen catheter 100. A user 601 is shown holding the device by hooking the middle finger in the second flange at 602, positioning the index finger along the side of syringe holder 306a and positioning the thumb on the thumb plate at 603. When the user presses on the thumb plate, the piston-like rod moves in parallel with the syringe plungers and each drug is uniformly delivered to one of the lumens in the catheter. The drugs do not mix until simultaneously injected into the patient's vein.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention.

What is claimed is:

1. A method for treating acute myocardial infarction complicated by advanced acute heart failure in a patient, comprising the steps of:
   securing at least two syringes prefilled with pharmacologically effective amounts of at least one beta-blocker that is esmolol, acebutorol, atenolol, betaxol, carteolol, carvedilol, esmolol, labetalol, landiolol, metoprolol, nadolol, nebivolol, oxprenolol, penbutolol, pindolol, propanolol, timolol and at least one positive inotropic agent that is amrinone, cilostazol, milrinone, enoximone, dobutamine, dobutamine, isoproterenol, epinephrine, levosimendan, into a device comprising:
   a body having a syringe holding portion;
   a syringe driving portion; and
   two or more syringes secured by the holding portion and the driving portion; and
   administering simultaneously the at least one beta-blocker and the at least one positive inotropic agent into a vein of said patient.

2. The method of claim 1, wherein said beta-blocker and positive inotropic agent do not mix before entering the patient's vein.

3. The method of claim 1, wherein the device further comprises:
   a multi-lumen catheter having a plurality of inlet channels and a single outlet channel comprising a plurality of lumens each of which is disposed in a watertight connection to one of the inlet channels; and
   a plurality of Luer-hubs each with a distal end connected to one of the inlet channels and with a proximal end connected to a syringe hub.

4. The method of claim 1, wherein said syringe holding portion comprises:
   a backboard having an open channel formed along a length of a bottom surface thereof;
   two or more syringe holders formed on a top surface of the backboard each having a shape to securely receive a syringe barrel therein;
   a flange-like motion stop disposed in perpendicular relation to a distal end of the backboard and extending upwardly from the top surface of the backboard and downwardly from a bottom surface of the backboard; and
   a first flange downwardly extending from the bottom surface of the backboard in parallel relation to and proximal to the downwardly extending motion stop.

5. The method of claim 4, wherein the flange-like motion stop forms a gap with each distal end of the syringe holders into which a barrel flange of the syringe is secured.

6. The method of claim 1, wherein the syringe driving portion comprises:
   a rod having a proximal end disposed within the open channel of a backboard and slidable therethrough; and
   a plunger clip disposed on a distal end of the rod configured to secure a thumb end of a syringe plunger.

7. The method of claim 6, wherein the plunger clip comprises:
   a thumb plate disposed on the distal end of the rod and perpendicular to a longitudinal axis of the rod; and
   a second flange extending upwardly from the rod in proximal and parallel relation to the thumb plate.

8. The method of claim 7, wherein the thumb plate and the second flange form a gap into which the thumb end of the plunger is secured.

9. The method of claim 7, wherein the second flange comprises a concavity at a lower end thereof configured to support a finger of a user of the device.

* * * * *